United States Patent [19]

Voss

[11] Patent Number: 4,861,330

[45] Date of Patent: Aug. 29, 1989

[54] CARDIAC ASSIST DEVICE AND METHOD

[76] Inventor: Gene Voss, 7614 Louis Pasteur, Suite 200, San Antonio, Tex. 78229

[21] Appl. No.: 24,986

[22] Filed: Mar. 12, 1987

[51] Int. Cl.$^4$ .............................................. A61B 19/00
[52] U.S. Cl. ....................................... 600/18; 604/53; 128/344
[58] Field of Search ............... 128/1 D, 344, 784–786, 128/419 P; 604/96, 49, 53; 600/18

[56] References Cited

U.S. PATENT DOCUMENTS

| | | | |
|---|---|---|---|
| 3,087,486 | 4/1963 | Kilpatrick | 128/642 |
| 3,266,487 | 9/1966 | Watkins et al. | 128/1 |
| 3,504,662 | 4/1970 | Jones | 128/1 |
| 3,692,018 | 9/1972 | Goetz et al. | 128/1 |
| 4,327,709 | 5/1982 | Hanson et al. | 128/1 |
| 4,346,598 | 8/1982 | Hanson et al. | 128/1 |
| 4,402,307 | 9/1983 | Hanson et al. | 128/1 |
| 4,467,790 | 8/1984 | Schiff | 128/1 |
| 4,475,560 | 10/1984 | Tarjan et al. | 128/785 |
| 4,515,587 | 5/1985 | Schiff | 604/96 |
| 4,527,549 | 7/1985 | Gabbay | 128/1 |
| 4,531,512 | 7/1985 | Wolvek et al. | 128/1 |
| 4,552,127 | 11/1985 | Schiff | 128/1 |
| 4,595,012 | 6/1986 | Webler et al. | 128/786 |
| 4,602,645 | 7/1986 | Barrington et al. | 128/786 |
| 4,664,114 | 5/1987 | Ghodsian | 128/344 |
| 4,685,446 | 8/1987 | Choy | 128/1 D |
| 4,771,765 | 9/1988 | Choy et al. | 600/18 |

OTHER PUBLICATIONS

The Journal of Thoracic and Cardiovascular Surgery, "Sustained Circulation by a Left Ventricular Balloon Pump after Severe Myocardial Damage in Dogs", by David E. Donald, Ph.D., Alfred A. Bove, M.D. and Dwight C. McGoon, M.D., vol. 63, No. 5, pp. 681–695, May 1972.

Primary Examiner—Dalton L. Truluck
Assistant Examiner—Denise Whelton
Attorney, Agent, or Firm—David G. Henry

[57] ABSTRACT

A device and method for assisting the pumping action of a failed heart. The device comprises an inelastic balloon, preferably conical in shape, connected to a catheter and pump. The balloon is percutaneously fed into a major blood vessel and then guided to a ventricle of the heart. When placed in the left ventricle, the balloon inflates during the isovolumetric contraction period before the aortic valve opens, and deflates after the aortic valve is closed but before the mitral valve has opened.

6 Claims, 4 Drawing Sheets

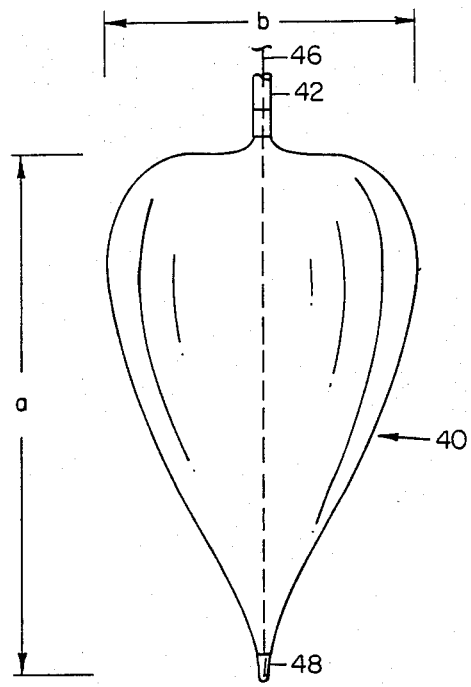
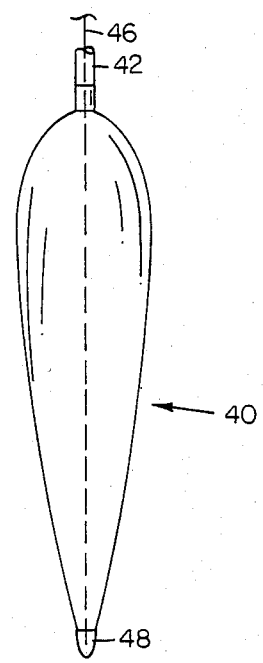
FIG. 3A    FIG. 3B
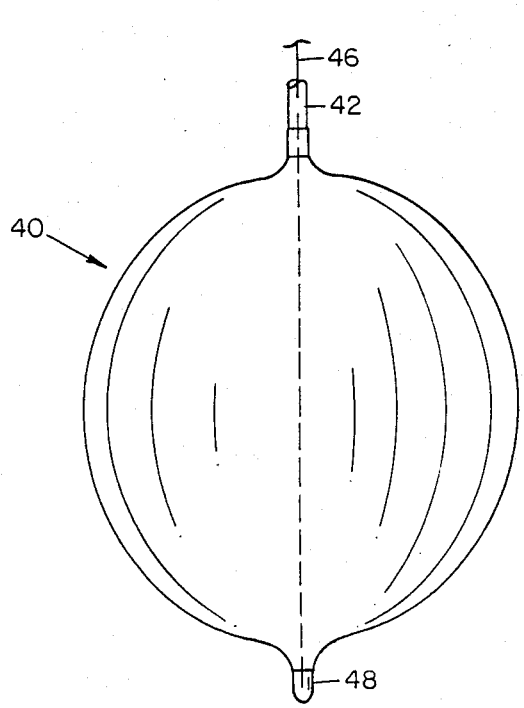
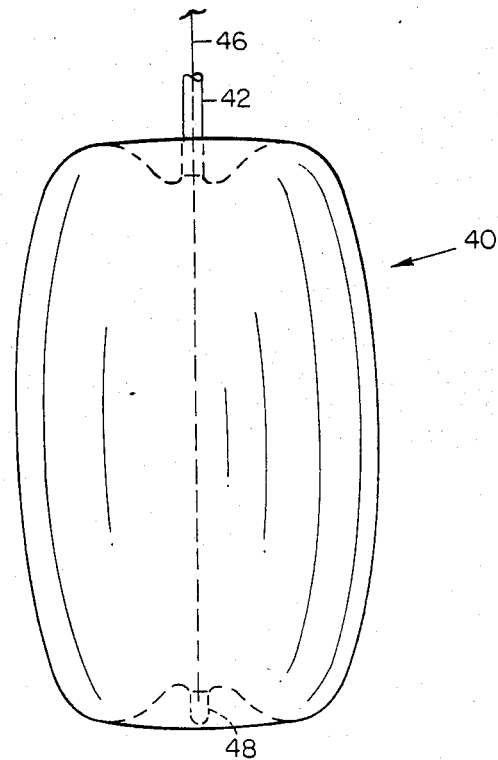
FIG. 3C    FIG. 3D

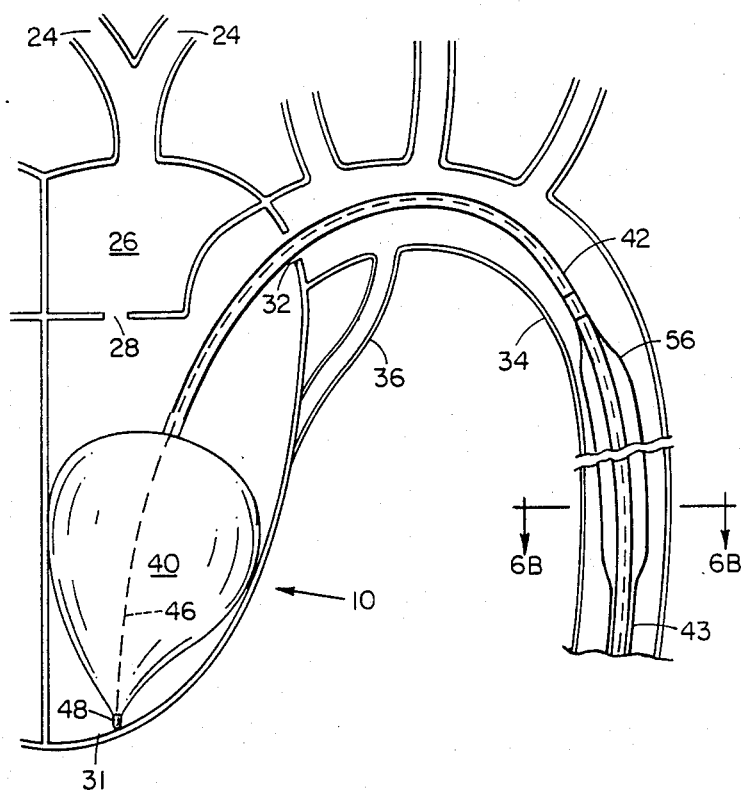
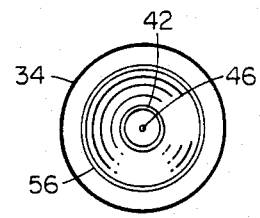
FIG. 6B
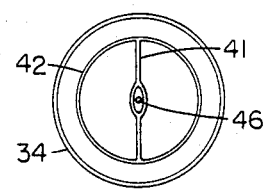
FIG. 6C
FIG. 6A
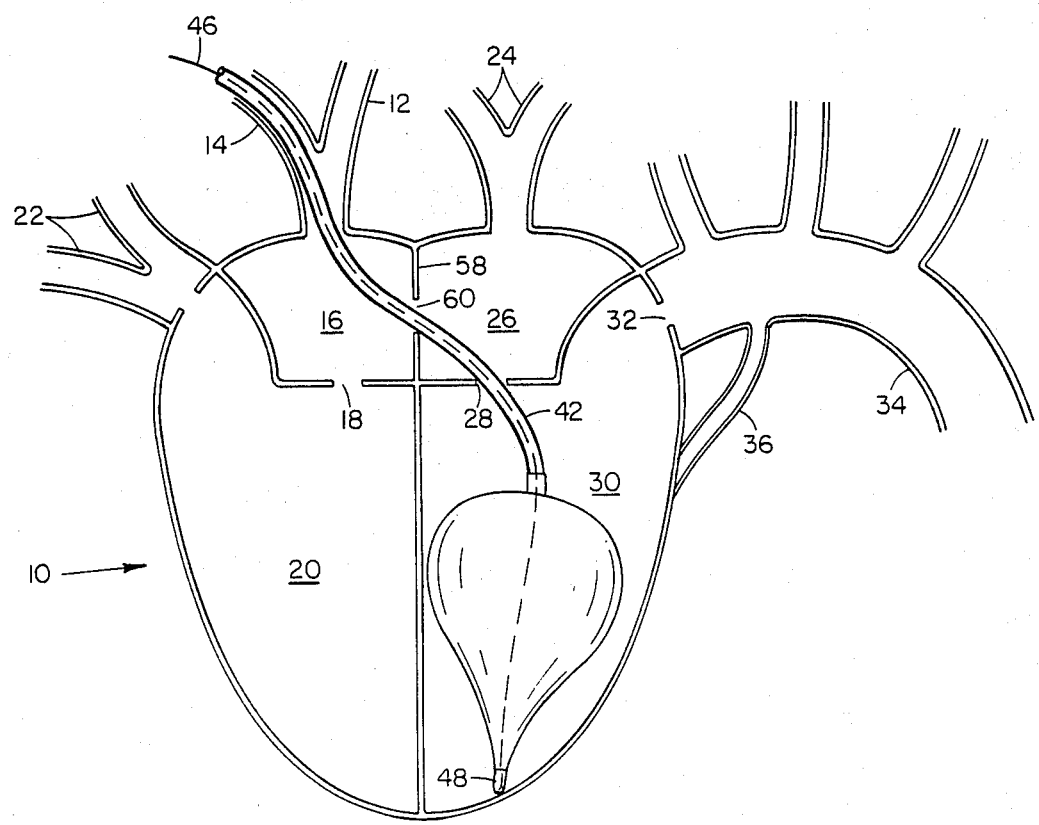
FIG. 7

CARDIAC ASSIST DEVICE AND METHOD

BACKGROUND OF THE INVENTION

1. Field of the Invention

The present invention generally relates to devices for assisting the pumping action of the heart, and more particularly to an inflatable balloon to be placed within the heart itself.

2. Description of the Prior Art

Heart disease is the number one killer among persons over 30. The most common manifestation of this disease is heart attack, or myocardial infarction. A heart attack is usually caused by clogging of the coronary arteries, those vessels which supply oxygen and nutrients to the heart itself, often due to an excessive accumulation of lipid material (fat) within the arterial walls (coronary occlusion or thrombosis).

A milder heart attack may result in mere "heart failure," characterized by an inability of the heart to pump blood at the rate needed to maintain adequate blood flow throughout the body. In this scenario, blood flow through the coronary arteries is appreciably diminished, but not totally cut off. This results in decreased blood flow (ischemia) to localized portions of the muscular tissues of the heart, with possible necrosis. Inadequacy of the coronary blood supply may give rise to chest pains (angina pectoris), and lead to shortness of breath (dyspnea) and the accumulation of excessive fluids (edema) in the lungs, liver, and lower limbs. The heart reacts by pumping more forcibly and faster, but this typically causes the ventricles to grow larger and become flaccid. Although the volume of the ventricle is increased, the maximum pressure during the isovolumetric period is actually lowered.

In the past, devices have been invented to serve some of the needs of heart failure patients. One important medical tool devised to assist the failing heart is the intra-aortic, or intra-arterial, balloon (IAB). The IAB is usually inserted into the body via the femoral artery near the groin, and threaded up to the aorta. An early IAB is disclosed in U.S. Pat. No. 3,504,662, issued to R. Jones. That device provides a peristaltic pumping action. Another IAB, providing uni-directional pumping, is described in U.S. Pat. No. 3,692,018, issued to Goetz et al. The balloon may be placed in the ascending or descending portions of the aorta, and more than one balloon may be employed, as depicted in U.S. Pat. No. 4,527,549, issued to S. Gabbay.

Numerous other advances have occurred in IAB technology. U.S. Pat. No. 4,327,709, issued to Hanson et al. describes an apparatus for percutaneous introduction of an IAB through a dilator-sheath. Special features of the balloon have also been devised. For example, U.S. Pat. No. 4,346,698, also issued to Hansen et al., discloses an IAB which has a stylet therein for rotating the IAB so as to twist and thereby decrease the diameter of the IAB during insertion. Improvements on this idea are discussed in U.S. Pat. Nos. 4,402,307; 4,467,790; and 4,531,512.

Basically, the IAB is designed to inflate immediately upon the closing of the aortic valve, thereby expelling blood from the aorta into the connecting arteries. The synchronous timing of the balloon is controlled by electrical signals from the heart, i.e., by monitoring the EKG of the patient. The tip of the balloon may even be equipped with an electrode to provide this function, as shown in U.S. Pat. No. 4,552,127, issued to P. Schiff.

All of the above devices, however, suffer one critical disadvantage in that they take for granted that the heart will be able to force a sufficient amount of blood into the aorta in the first place. Where the efficiency of cardiac output is severely affected by myocardial stretching, systemic blood pressure can drop from 130/80 to as low as 50/30. In such cases, an intraaortic balloon is, at best, a band-aid remedy.

It would therefore be desirable and advantageous to devise an intraventricular balloon to assist the pumping action of the heart. No such device yet exists, although an article by Donald et al., published in the *Journal of Thoracic and Cardiovascular Surgery*, vol. 63, no. 5 (May 1972), discusses open heart experiments employing a cardiac balloon pump on a dog.

SUMMARY OF THE INVENTION

Accordingly, the primary object of the present invention is to provide a device for assisting the pumping action of the human heart.

Another object of the invention is to provide such a device which will actually be placed within the heart.

Still another object of the invention is to provide a method of employing such a device.

Yet another object of the invention is to provide a method of percutaneous retrograde introduction of the device into the heart.

The foregoing objects are achieved in a cardiac assist device comprising an intra-ventricular balloon and support system. The intra-ventricular balloon may be introduced into either the left or right ventricles via the femoral artery or vein, respectively, or may pass through the atria to the left ventricle. Additional intra-aortic balloons may be used in conjunction with the intraventricular balloon.

BRIEF DESCRIPTION OF THE DRAWINGS

The novel features believed characteristic of the invention are set forth in the appended claims. The invention itself, however, as well as a preferred mode of use, further objects and advantages thereof, will best be understood by reference to the following detailed description of illustrative embodiments when read in conjunction with the accompanying drawings, wherein:

FIGS. 3A–3D show various embodiments of the balloon itself.

FIG. 6A is also similar to FIG. 4B, but it additionally depicts an intra-aortic balloon working in conjunction with the ventricular balloon; FIG. 6B shows a cross-section taken along lines 6B—6B of FIG. 6A; FIG. 6C shows an analogous cross-section of an alternative embodiment.

FIG. 7 shows an alternative method of placement of the balloon within the left ventricle, the catheter passing through the left and right atria.

DESCRIPTION OF THE PREFERRED EMBODIMENTS

Figure 1:
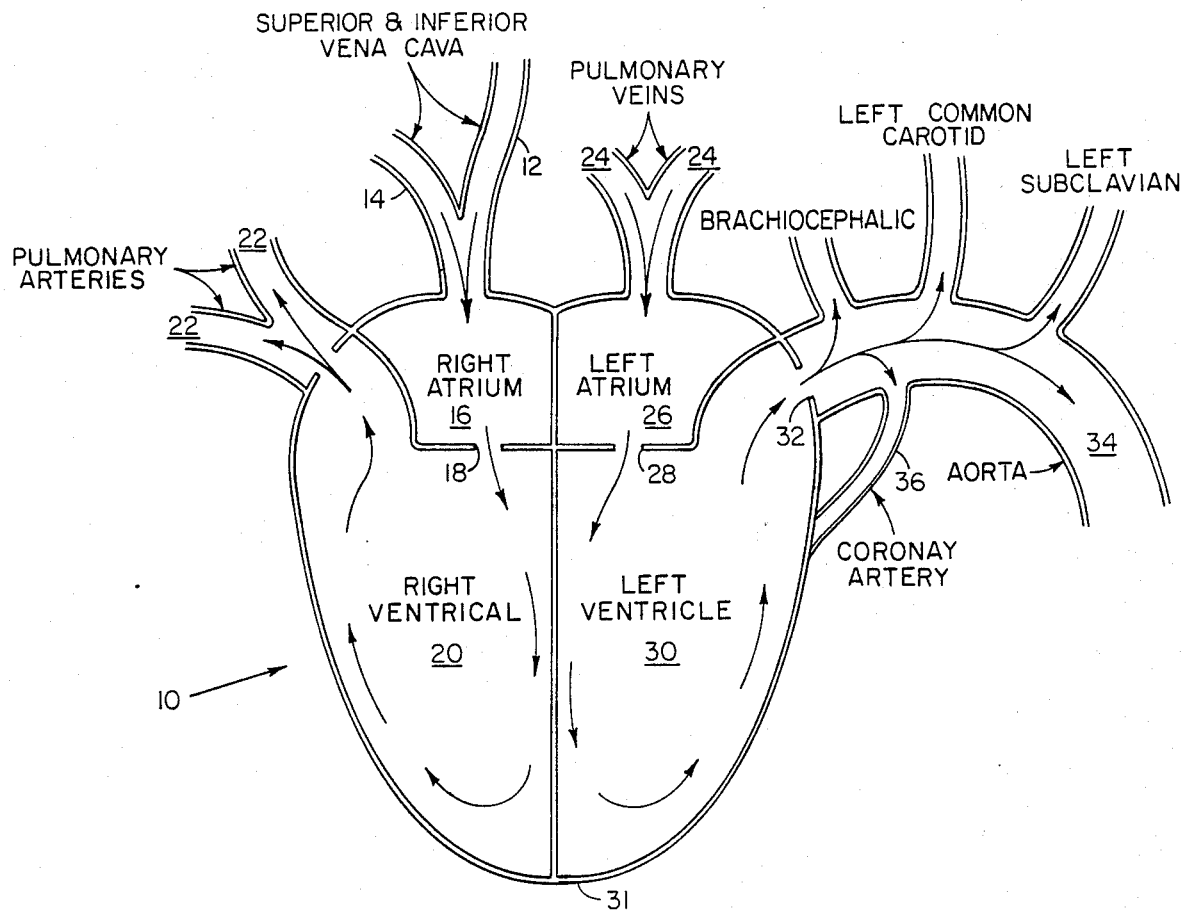
FIG. 1 is a schematic diagram of the heart showing cardiac blood flow.

With reference now to the FIGS., and in particular with reference to FIG. 1, there is depicted a schematic diagram of the human heart 10. Blood flow is detailed by directional arrows. It should be understood that all of the figures only schematically depict the heart, as these diagrams are not physically accurate.

Before discussing the structure and operation of the invention, a brief explanation of cardiac hemodynamics is necessary. Cardiac blood flow may be said to begin at the juncture of the superior and inferior venae cavae, 12 and 14 respectively, where all oxygen-depleted blood in the body is forced into the right atrium 16. The natural pumping action of the heart draws the blood through the tricuspid (atrioventricular) valve 18 into the right ventricle 20. Right ventricle 20 then drives the blood to the lungs via pulmonary arteries 22. Oxygenated blood returns from the lungs to the heart by way of pulmonary veins 24 which lead into the left atrium 26, passing then through mitral (bicuspid) valve 28 into the left ventricle 39. Contraction of left ventricle 30 forces the blood into aorta 32 which then distributes the blood throughout the body.

The ventricle walls are generally thicker than the walls of the atria, necessary for pumping the blood against the pressure in the arteries. The left ventricular wall is even thicker than the right ventricular wall, the bulk of the wall comprising the myocardium, being thick bands of muscular tissue. The left ventricle is the most critical component of the heart as it provides the maximum pressure during the systolic phase of the cardiac cycle to power the entire circulatory system. Because of its thicker nature, and its increased workload, it is usually the myocardial layer of this ventricle that suffers necrosis or ischemia during a heart attack. For this reason, it is anticipated that the intra-cardial balloon will most often be placed within a suffering left ventricle.

Figure 2:
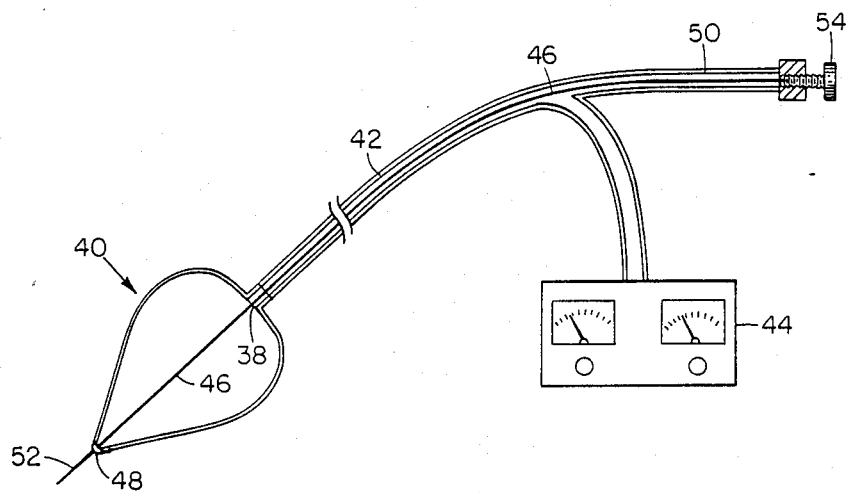
FIG. 2 is a cross-sectional view of the intra-ventricular balloon and catheter, also showing the supporting pump system.

The balloon itself as well as the supporting pump system is generally represented in FIG. 2. Balloon 40 is located at the distal end of a catheter 42 which in turn is connected to pump 44. A wire or stylet 46 runs from the tip 48 of balloon 40 through aperture 38 and catheter 42 and diverges therefrom into branch tube 50. Tip 48 of balloon 40 may be equipped with a needle 52 for securing the balloon within the ventricle, as discussed below. Stylet 46 terminates at knob 54 which may be used to twist stylet 46 as described in U.S. Pat. No. 4,346,698, which is hereby incorporated for all purposes. Twisting stylet 46 is desirable to minimize the effective diameter of the deflated balloon 40 as it is inserted into the body. Stylet 46 also provides structural integrity for balloon 40.

Balloon 40 is preferably conical shaped to correspond to the shape of the inner wall (endocardium) of the ventricle. It should be made of an inelastic, nonthrombogenic material, such as polyvinyl chloride. The volume of balloon 40 should be between 10 and 80 milliliters, but is dependent on many factors, such as the impedance of flow out of the aorta. A higher impedance would require a higher balloon volume. The balloon volume is also dependent on the tone of the ventricle. Good myocardial tone would require a small balloon, say 15 ml., but if the ventricle were highly distended (or highly distendable) a larger balloon, e.g., 60 ml., might be necessary. Similarly, an aneurismal dilation within the ventricle would require a larger balloon. As a general rule, the balloon size should never be less than twenty-five percent (25%) of the left ventricular end diastolic volume.

Balloon 40 may come in many different shapes, as can be seen by reference to FIGS. 3A–3D. As previously mentioned, balloon 40 is preferably conical, as shown in FIG. 3A, having a length a between 3 and 6 centimeters, and a width b at the base between 2.5 and 5 centimeters, depending on the desired volume. For example, a balloon having a volume of 50 ml. would have an approximate length of 5 cm and a width of 4 cm. Other shapes include a slender balloon (FIG. 3B), spherical (FIG. 3C), or "bell pepper" shaped (FIG. 3D) where the tip 48 is somewhat recessed.

Balloon pump 44 must be capable of inflating and deflating balloon 40 with a time period of about 100 milliseconds. This is critical as the balloon 40 should be completely inflated during the isovolumetric period of ventricular contraction (about 45 ms.), and deflated while aortic valve 32 is still open. The balloon 40 should be deflated while aortic valve 32 is still open in order to avoid obstruction of blood outflow. Of course, the inflation/deflation cycle is dependent upon the specific characteristics of each individual heart. The inflation/deflation period may actually be anywhere from 50 to 200 milliseconds.

Pump 44 must provide pressures of 150 millimeters of mercury or more. Timing of the inflation-deflation cycle may be accomplished by coordination with the EKG of the heart (i.e., beginning inflation using the Q-R-S event of the PQRST signal). An electrode may actually be placed on tip 48 of balloon 40 for this purpose, as disclosed in U.S. Pat. No. 4,552,127. For a more thorough discussion of balloon pumps and their activation, see U.S. Pat. No. 3,266,487, which is hereby incorporated for all purposes. In practice, a balloon pump produced by the Datascope Corp. of Oakland, N.J., Model No. 9000 is satisfactory for these purposes. Although any relatively inert gas may be used to pump balloon 40, helium is preferred as its lower viscosity is more suited for the short inflation-deflation cycles involved here.

Catheter 42 has an outer diameter between 4 and 12 french, preferably about 8 french. As it is typically inserted near the groin, it should be from 50 to 80 centimeters long. Excess length is undesirable as increases pump resistance. The catheter 42 may be made of polyurethane, or coated with some nonthrombogenic substance such as heparin.

PROCEDURE

The technique for initial insertion of the ventricular balloon into the body is generally the same as previously known. As discussed in U.S. Pat. No. 4,327,709, which is hereby incorporated for all purposes, a puncture is made in the patient's skin, subcutaneous tissue, and major blood vessel, usually the femoral artery. A cannula may be inserted into the puncture to facilitate guiding balloon 40 and catheter 42 into the artery. The balloon 40 is then threaded upwards within the artery toward heart 10. This procedure is known as percutaneous retrograde introduction.

The skilled surgeon will know when the balloon 40 is nearing heart 10. At this time, radiopaque dye may be injected into the left ventricle in order to assist the passage of balloon 40 through aortic valve 32. The surgeon may anticipate the opening of aortic valve 32 by the EKG of the patient, and thereby discern when to apply longitudinal pressure to the exposed portion of catheter 42. Of course, balloon 40 is kept deflated during this portion of the procedure.

Figure 4A:
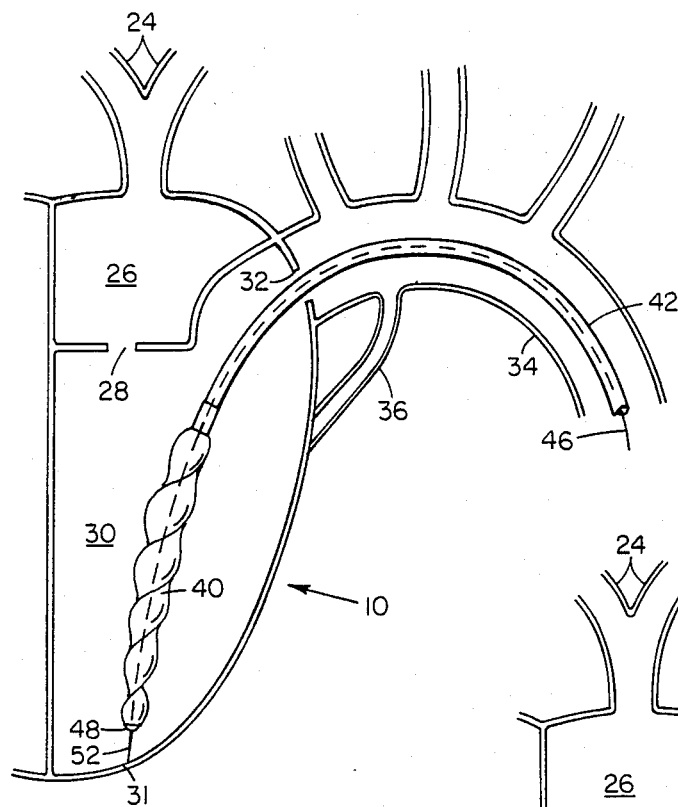
FIG. 4A is cross-sectional representation of the left ventricle of the heart with the deflated balloon therein.
Figure 4B:
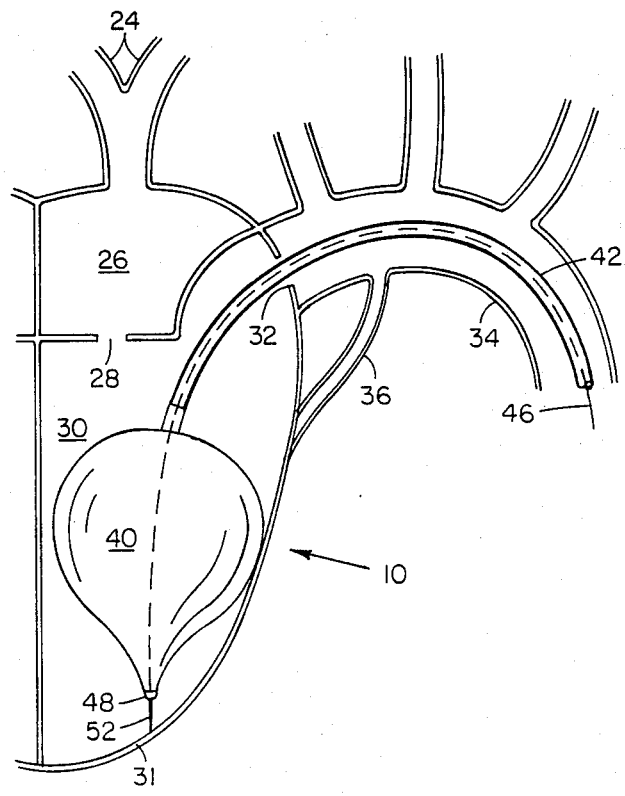
FIG. 4B shows the balloon inflated.

After balloon 40 has passed through aortic valve 32, the tip 48 of balloon 40 is preferably placed at the apical dimple 31 of left ventricle 30, as depicted in FIG. 4A. Placement of balloon 40 near apical dimple 31 allows balloon 40 to roll up along the ventricular wall, thus minimizing damage to the endocardium and avoiding entrapment of blood between balloon 40 and the ventricular wall. Balloon 40 may be securely fixed to the apical dimple by means of a needle 52 placed at the tip 48 of balloon 40. Needle 52 may be in the shape of a hook, so as to be essentially permanently lodged within the endocardium, or alternatively, it may straight. In the latter case, it is envisioned that the needle 52 may actually pierce the wall of heart 10, including the pericardium, and that it may be secured external to heart 10 in thoracic surgery. In any event, needle 52 is not essential to the operation of balloon 40 as sufficient longitudinal force along catheter 42 compels the tip 48 of balloon 40 to the apical dimple 31. With balloon 40 in place, pump 44 may be activated. The inflated balloon is depicted in FIG. 4B.

The normal size of the left ventricle 30 of an adult human heart varies from about 100 ml. to 175 ml. The amount of blood exiting the left ventricle of a healthy person during systole is about 60% of this volume. Taking as an example an individual whose ventricular volume is about 125 ml., we might say that about 75 ml. of blood flows into the aorta in one cardiac cycle. In a failed heart, 25% or less of the ventricular volume is ejected, e.g., 30 ml. It is anticipated that use of intraventricular balloon 40 will increase the cardiac output in such a case by at least 50%, and probably 100% or more. The total amount of blood ejected will at least equal the volume of the balloon, say 50 ml. for the above facts. It is important to note, however, that the volumetric displacement of balloon 40 is not as meaningful as the increased ventricular pressure caused by the inflation thereof during the isovolumetric contraction period. It is this increased pressure that significantly contributes to cardiac output.

In more serious cases, the ventricle may become distended, resulting in a volume of up to 250 ml., but in such a case, the ventrical loses much of its pumping ability and as little as 5% of this volume is ejected. Intra-ventricular balloon 40 is most effective in these cases; a 75 ml. balloon could raise cardiac output from 15 ml. to 80 ml. or more. Although regurgitation through aortic valve 32 is likely due to the presence of catheter 32 therein, it is anticipated that no more than 10% of the gross blood flow will be so regurgitated. Thus intra-ventricular balloon 40 has clear advantages over prior art devices. Furthermore, the increased systolic pressure contributes to enhanced blood flow in coronary artery 36. This can actually revitalize the heart in cases where the myocardium suffers from localized ischemia rather than necrosis.

Figure 5:
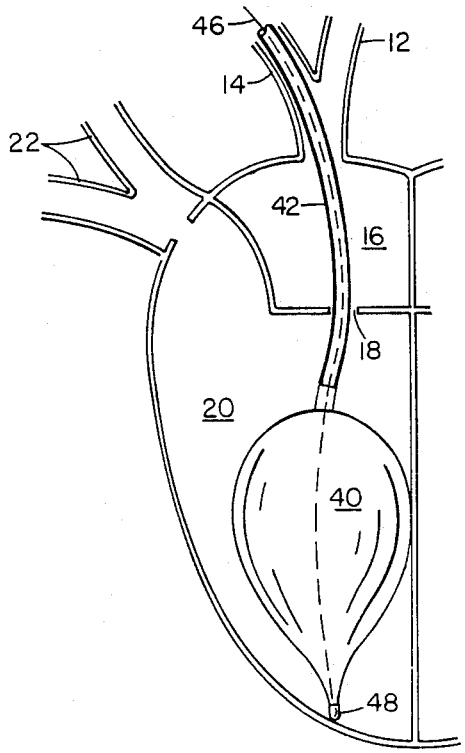
FIG. 5 is similar to FIGS. 4A and 4B, but it depicts the balloon located within the right ventricle.

Use if intra-ventricular balloon 40 is not limited to the left ventricle, but may also be used in right ventricle 20. Most cases of heart failure are due to myocardial infarction of the left ventricle, but in cases where the right ventricle is damaged or becomes distended, placement of balloon 40 within right ventricle 20 will augment blood flow, especially pulmonary circulation. As depicted in FIG. 5, balloon 40 and catheter 42 may be inserted in the femoral vein and maneuvered to inferior vena cava 14. In a manner similar to that described above, balloon 40 is then pushed into right atrium 16, through tricuspid valve 18, and finally into right ventricle 20. Balloons could even be placed in both the left and right ventricles.

Intra-ventricular balloon 40 may be used alone or in conjunction with other prior art intra-aortic balloon. FIG. 6A shows such apparatus. Here, intraventricular balloon 40 has been placed in left ventricle 30, and a second aortic balloon 56 is positioned in the descending aorta. An intraventricular balloon 40 and intra-aortic balloon 56 must be inflated asynchronously, separate airways must be provided to pump 44. FIG. 6B depicts one way in which this may be done. In this embodiment, an outer catheter 43 surrounds catheter 42. Outer catheter 43 terminates where intra-aortic balloon 56 begins, while catheter 42 continues within balloon 56 and leads to intra-ventricular balloon 40 within the heart. The preferred design for such an arrangement, however, is shown in FIG. 6C where catheter 42 is divided into two airways by partition 41. Stylet 46 may run inside partition 41, and one airway simply opens and terminates at intra-aortic balloon 56.

Another method of using intra-ventricular balloon 40 is shown in FIG. 7. In some instances, the femoral artery may be undesirable for percutaneous retrograde insertion, or the aortic valve 32 may have been damaged to the extent that placement of a catheter therein would be fatal. In such a case, the left ventricle may actually be reached via the right atrium. There is a thin layer in the septum 58 dividing the atria known as the foramen ovale. Foramen ovale 60 begins as an aperture in the fetal heart until the middle period of fetal life. It then grows a fold from the posterior wall which acts as a sort of valve, allowing blood to pass only from the right to the left atrium. The balloon and catheter are again threaded through the femoral vein to inferior vena cava 14, into right atrium 16, and through foramen ovale 60 into left atrium 26. From there it passes through mitral valve 28 into left ventricle 30 where it is secured as discussed above. Obviously this technique is less desirable as it has more complications than introduction via the femoral artery.

It is believed that the primary use of this technique will be temporary in nature, for those patients whose hearts have failed to the point that they must be kept on some sort of external life support system while awaiting a heart transplant. It is conceivable, however, that once implanted, the cardiac assist device as disclosed could be made portable and somewhat permanent.

Although the invention has been described with reference to specific embodiments, this description is not meant to be construed in a limiting sense. Various modifications of the disclosed embodiment, as well as alternative embodiments of the invention will become apparent to persons skilled in the art upon reference to the description of the invention. It is therefore contemplated that the appended claims will cover such modifications that fall within the true scope of the invention.

I claim:

1. A method of assisting the pumping action of a heart, comprising the steps of:
    inserting a balloon member into the femoral vein, said balloon member joined in fluid communication to a catheter member;

guiding said balloon member and said catheter member within said femoral vein toward said heart, into the inferior vena cava and the right atrium;

pushing said balloon member past the foramen ovale into the left atrium and past the mitral valve into the left ventricle of said heart; and activating pump means connected to said catheter member whereby said balloon member is inflated during each contraction of said ventricle, and deflated shortly thereafter.

2. The method of claim 1 further comprising the step of placing said balloon member at the apical dimple of said left ventricle.

3. The method of claim 2 further comprising the step of securing said balloon member to the inner wall of said left ventricle by needle means attached to a tip of said balloon member.

4. The method of claim 3 further comprising the step of injecting a radiopaque dye into said ventricle before pushing said balloon member therein.

5. The method of claim 1 further comprising the step of securing said balloon member to the inner wall of said left ventricle by needle means attached to a tip of said balloon member.

6. The method of claim 1 further comprising the step of injecting a radiopaque dye into said ventricle before pushing said balloon member therein.

* * * * *